United States Patent [19]

Baumgärtel

[11] Patent Number: 4,531,816
[45] Date of Patent: Jul. 30, 1985

[54] SPACING SAFETY MECHANISM FOR OPERATION MICROSCOPES WITH ELECTROMOTIVE STANDS

[75] Inventor: Patrice Baumgärtel, Roquevaire, France

[73] Assignee: Carl-Zeiss-Stiftung, Heidenheim on the Brenz, Fed. Rep. of Germany

[21] Appl. No.: 516,309

[22] Filed: Jul. 22, 1983

[30] Foreign Application Priority Data

Feb. 4, 1983 [DE] Fed. Rep. of Germany ... 8302999[U]

[51] Int. Cl.³ .......................... G02B 21/00; G05B 9/02
[52] U.S. Cl. ..................................... 350/521; 350/507; 318/460
[58] Field of Search ...................... 350/507, 521, 530; 318/460; 250/201 AF, 201; 340/104

[56] References Cited

U.S. PATENT DOCUMENTS 3,809,454 5/1974 Brambring ........................... 350/521
4,125,826 11/1978 Rasmussen et al. .................. 340/63

Primary Examiner—Jon W. Henry
Attorney, Agent, or Firm—Stonebraker, Shepard & Stephens

[57] ABSTRACT

A spacing safety mechanism for operation microscopes with electromotive stands is described, in which ultrasonic transmitter and an ultrasonic receiver are arranged in the vicinity of the operation microscope. When the travel time of the ultrasonic signals reflected by the body of the patient is less than a predeterminable value, the voltage supply of the motor for the downward movement of the operation microscope is interrupted.

9 Claims, 9 Drawing Figures

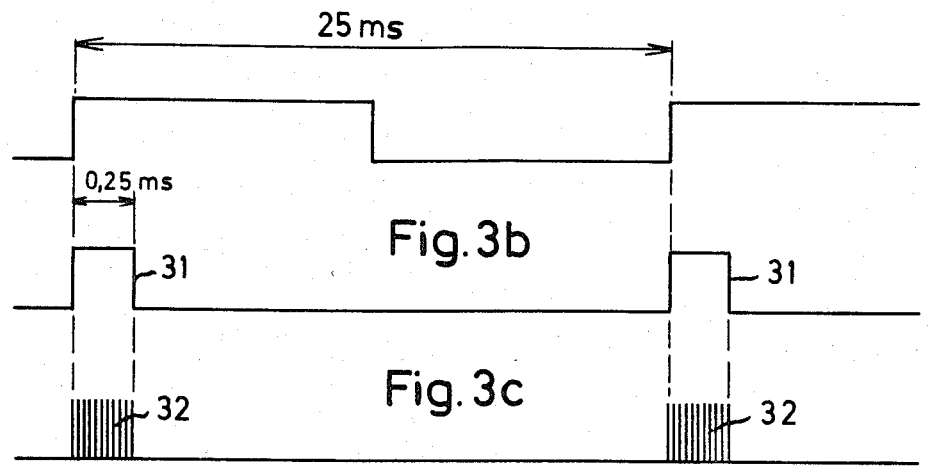
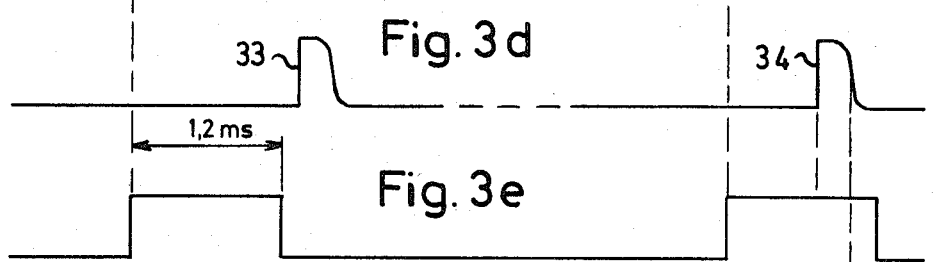
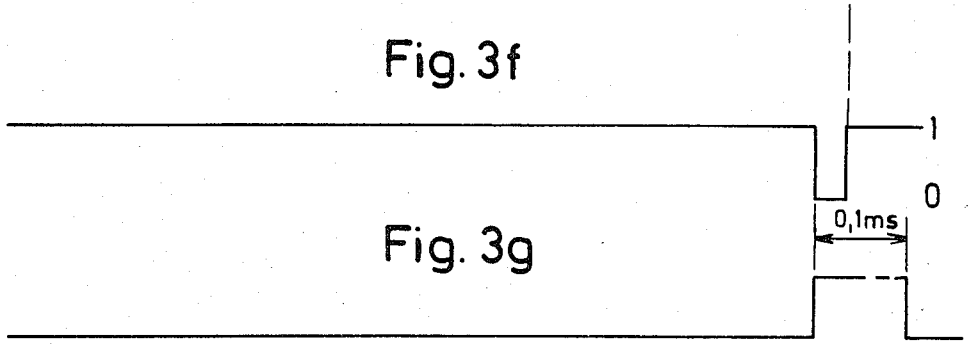

SPACING SAFETY MECHANISM FOR OPERATION MICROSCOPES WITH ELECTROMOTIVE STANDS

SUMMARY OF THE INVENTION

The present invention relates to a spacing safety mechanism for an operation microscope with an electromotive stand.

Operation microscopes having an electromotive stand are used in numerous fields of medicine, for instance in ophthalmology and microsurgery. The advantage of electromotive stands over normal stands is not merely that changes in position of the operation microscope can be effected more easily by the doctors and nurses but also that the operators need not come into contact with the non-sterile parts of the stand, and that large parts of the stand need not be made sterile.

In the case of such stands with motor drives there is the danger that the operation microscope will come too close to the patient as a result of erroneous or negligent operation of the motor drive.

It is therefore absolutely necessary to prevent having the patient clamped between the operating table and the operation microscope.

A continuously adjustable spacing safety device for an electromotive ceiling stand is known (see for instance Carl Zeiss publication 30-058-d) which operates with mechanical limitation of the displacement by a pull rope which is installed in the ceiling column.

This limiting of the stroke, however, has the disadvantage that it must be set before each operation as a function of the height of the operating table and in accordance with the specific height of the site of the operation.

The object of the present invention is to provide a spacing safety mechanism for an operation microscope with electromotive stand which operates properly for every height of the operating table and of the specific site of the operation without any adjustments having to be previously effected.

This object is obtained in accordance with the invention by providing an ultrasonic transmitter arranged in the vicinity of the microscope and an ultrasonic receiver also arranged in the vicinity of the microscope, and by an electronic unit, arranged on the stand and cooperating with its motor drive, for producing a signal for the ultrasonic transmitter and processing the signals from the ultrasonic receiver.

In one advantageous embodiment, the ultrasonic transmitter and ultrasonic receiver are arranged on the bottom side of the microscope body, preferably on opposite sides thereof.

It is particularly advantageous to integrate the ultrasonic transmitter and ultrasonic receiver in the microscope body and to integrate the electronic unit in the stand. Such an embodiment enters into consideration in particular, for new instruments. An arrangement with the components on the outside is favorable for the refitting of already existing instruments.

BRIEF DESCRIPTION OF THE DRAWINGS

The invention will be explained in further detail with reference to an illustrative embodiment shown in the accompanying drawings, in which:

FIGS. 3a to 3g are time graphs showing the manner of operation of the circuit shown in FIG. 2.

DESCRIPTION OF THE PREFERRED EMBODIMENT

Figure 1:
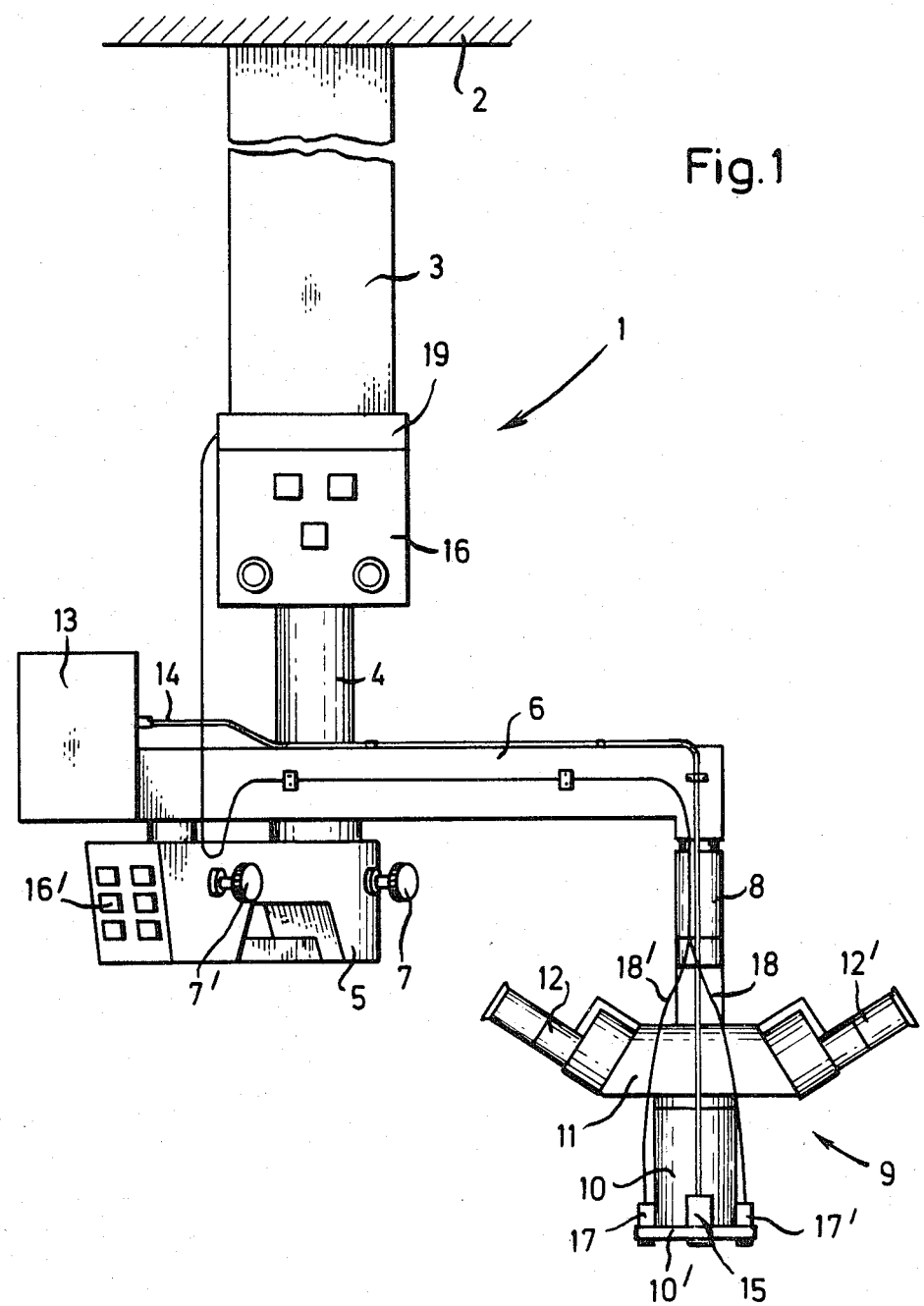
FIG. 1 is an overall side elevational view of an operation microscope supported from a ceiling stand and provided with the new spacing safety mechanism of the present invention.

In FIG. 1, a known ceiling stand is indicated in general by the numeral 1. Fastened to the ceiling 2 is a ceiling column 3, within which the stand column 4 is moved in a direction perpendicular to the ceiling (i.e., vertically) by a motor drive arranged within the ceiling column. The horizontal arm 5 is arranged for horizontal swinging movement on the lower end of the stand column 4, and in its turn it supports the horizontally swingable carrier arm 6. The horizontal arm 5 and the carrier arm 6 are manually brought into the desired position and then fixed therein by the clamping screws 7 and 7'. The operation microscope indicated in general at 9 is fastened via the coupling member 8 to the outer end of the carrier arm 6. The microscope includes the microscope body 10, the beam-splitter 11, and the eyepieces 12 and 12', through which two different persons may simultaneously observe the operation site. On the other end of the carrier arm 6 there is mounted the lamp housing 13 which furnishes light through the light guide 14 to the illuminating device 15 on the microscope. The usual control panels of the known ceiling stand are shown at 16 and 16'.

In accordance with the present invention, the ultrasonic transmitter 17 and the ultrasonic receiver 17' are arranged, in the embodiment shown, on the bottom side 10' of the microscope body 10. Ultrasonic transmitter 17 and ultrasonic receiver 17' can, however, also be attached to some other suitable part, for instance to a slit lamp or a part which is connected directly to the carrier arm 6. The ultrasonic transmitter 17 and receiver 17' can also be integrated in the microscope body and therefore be included in its housing.

It is advantageous to arrange the ultrasonic transmitter 17 and receiver 17' at a certain distance apart so that no sound waves can pass directly from the ultrasonic transmitter 17 to the ultrasonic receiver 17'. This can furthermore be facilitated by components which have a directional characteristic. The ultrasonic pulses coming from the ultrasonic transmitter 17 are reflected in part by the body of the patient and their echo impinges on the ultrasonic receiver 17'. The travel time of the ultrasonic pulses is therefore a direct measure of the distance between ultrasonic transmitter 17 and ultrasonic receiver 17', on the one hand, and the body of the patient, on the other hand.

The ultrasonic transmitter 17 and ultrasonic receiver 17' are connected by the cables 18 and 18' to the electronic unit 19 which is arranged on the ceiling column 3 in the embodiment shown in the drawing. However, the electronic unit 19 could also be integrated in the ceiling stand, i.e. installed in its housing. The electronic unit 19, in addition to containing the signal production for the ultrasonic transmitter 17 and the signal processing for the ultrasonic receiver 17', also contains the voltage supply for two relays, one of which is arranged in the voltage supply for the downward movement of the motor for the stand column 4. A second relay can possibly be arranged in the voltage supply for the upward movement of the operating table. If the distance between ultrasonic transmitter 17 and receiver 17' and the body of the patient becomes too small, i.e. if the ultrasonic pulses coming from the ultrasonic transmitter 17 return to the ultrasonic receiver 17' within too short a period of time, further reduction in the distance between operation microscope and operating table is prevented by the said relays, while an increase in the spacing is possible at any time.

Figure 2:
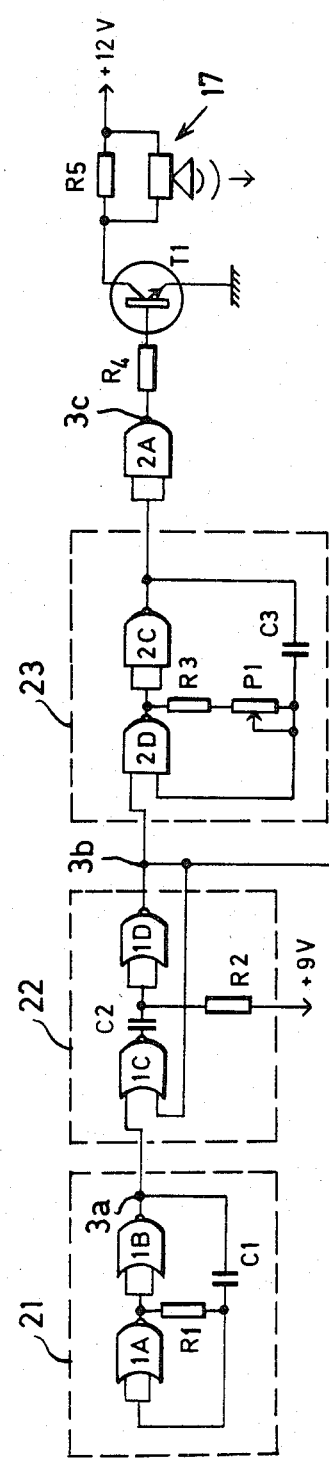
FIG. 2 is a circuit diagram for the production and processing of the ultrasonic signal.
Figure 2:
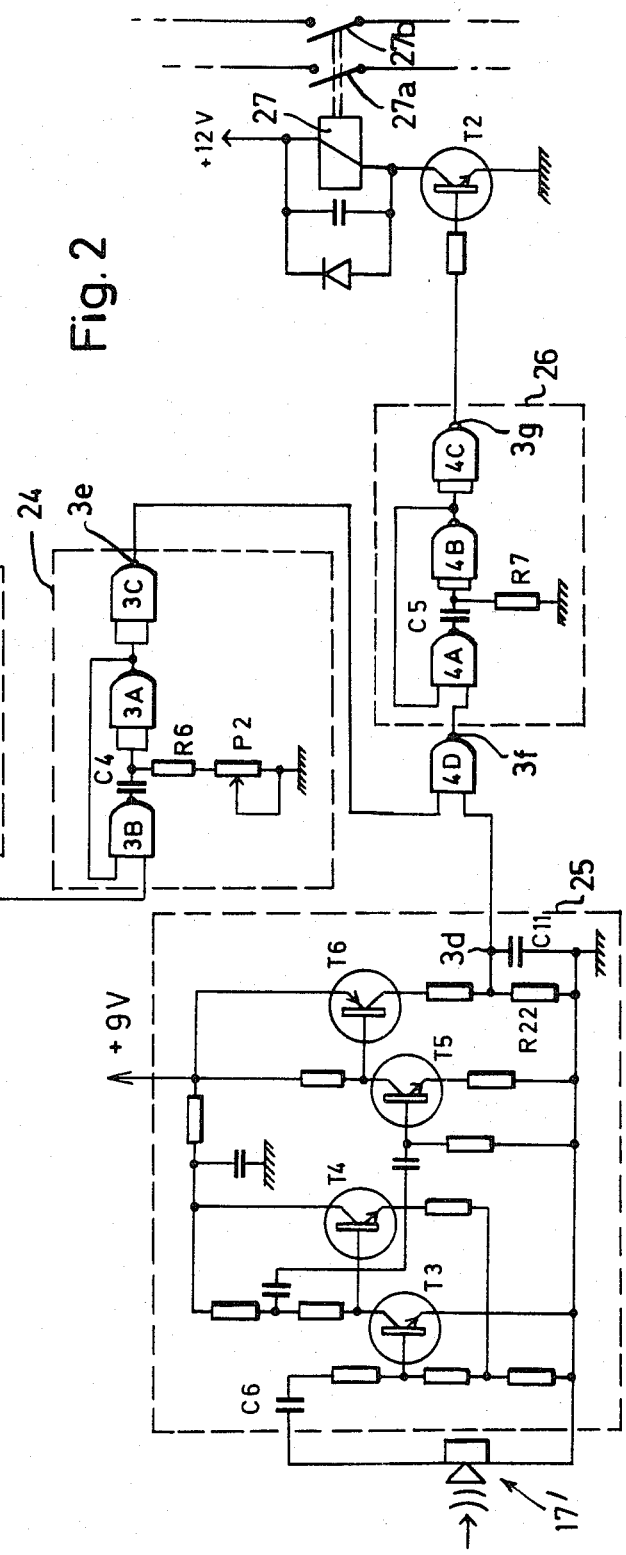

FIG. 2 shows an embodiment of the circuit arrangement contained in the electronic unit 19 for the producing and processing of the ultrasonic signal. A known oscillator circuit 21 comprises the NOR gates 1A and 1B, the resistor R1, and the capacitor C1. R1 and C1 determine the frequency of the square oscillation, shown in FIG. 3a, which is present at the circuit point 3a. In one advantageous embodiment, this frequency is 40 Hz. From the upward sides of this oscillation which follow each other at intervals of 25 ms, square pulses, designated 31 in FIG. 3b, are produced at the circuit point 3b in the known monostable assembly 22 which comprises the NOR gates 1C and 1D, the 0.25 ms duration of said pulses being determined by the capacitor C2 and the resistor R2.

For the duration of these square pulses the oscillator 23 oscillates. It is developed in known manner from the NAND gates 2D and 2C and its frequency of about 40 kHz is determined by the resistor R3, the variable potentiometer P1, and the capacitor C3. Behind the NAND gate 2A which serves as an inverter, there is thus present at the circuit point 3c the voltage course shown in FIG. 3c, with which the individual voltage pulses have a time spacing of 0.025 ms so that there are ten voltage pulses within the time interval of 0.25 ms. The ultrasonic transmitter 17 is supplied with the signals 3c produced in this way via the resistor R4, the transistor T1 and the resistor R5. The ultrasonic transmitter 17 therefore emits ultrasonic signals of a duration of 0.25 ms and a frequency of 40 kHz at intervals of about 25 ms.

As ultrasonic transmitter 17 a MURATA MA-40 L1-S can be used, for instance. As ultrasonic receiver 17' the MURATA MA-40 L1-R is suitable. Both of them have a small bandwidth of 40 kHz ±1 kHz with −3 dB, which, to be sure, requires an exact setting of the transmitter frequency but results in high selectivity and thus great assurance against interference.

The echo signals received by the ultrasonic receiver 17' are amplified in the known integration amplifier 25 which suppresses low frequencies which may come from mechanical oscillations. In the first stage of the amplifier, the high ohmic character of the receiver 17' which is coupled capacitively via the capacitor C6 is adapted to the low ohmic character of the output by the transistors T3 and T4. In the second stage, the signal is amplified by the transistors T5 and T6. The RC member consisting of R22 and C11 produces an integration of the individual ultrasonic signals.

At the output of the integration amplifier 25, which is designated in FIG. 2 by the circuit point 3d, echo signals, such as shown in FIG. 3d, are then present. For the further processing the decisive factor is now what the time interval is between the echo signals and the emitted ultrasonic signals corresponding to them. Since the individual ultrasonic signals are 25 ms apart, which corresponds to a distance of 4 meters, there is no difficulty as to the ascription of the echo signals. Furthermore, multiply reflected signals are too weak to still produce any effects with the signal processing described here.

Further reduction in the distance between the patient and the microscope 9 must be prevented when this distance becomes less than, for instance, 20 cm. This corresponds to a path between ultrasonic transmitter 17 and ultrasonic receiver 17' of 40 cm and a time difference of 1.2 ms. If the echo returns in less than this time, the spacing safety mechanism must respond. For this purpose the logic level 1 shown in FIG. 3e is produced at the corresponding end of the ultrasonic signals, namely by the downward sides of the signal for 1.2 ms which is shown in FIG. 3b and is present at the circuit point 3b. The monostable assembly 24 provided for this purpose comprises the NAND gates 3B and 3A, the inverter 3C, the capacitor C4, the resistor R6 and the potentiometer P2, the time of 1.2 ms being established by the three last-mentioned parts.

The output of this monostable assembly 24 is connected to the output of the integration amplifier 25 by the NAND gate 4D. The condition present at its output 3f is shown in FIG. 3f with reference to FIGS. 3d and 3e. The echo signal 33 lies outside the 1.2 ms after the end of the ultrasonic signal 32; the logic level 1 remains unchanged at the circuit point 3f. The echo signal designated 34, on the other hand, lies within the 1.2 ms and thus the logic level 0 is produced at the circuit point 3f during the echo signal. (A signal corresponding to a considerably shorter distance cannot of course be present already 25 ms later but only at a much later time; for this reason, the course of the signal between the two echo signals is shown in dashed line.)

The logic level 0, which is possible only during the brief echo signal, is lengthened by the monostable assembly 26 to 0.1 seconds. This monostable assembly again comprises two NAND gates 4A and 4B and capacitor C5 and resistor R7 by which the time is established. The NAND gate 4C acts as an inverter so that in the event of an echo within 1.2 ms a logic level 1 for 0.1 s is present at the circuit point 3g. In this way the relay 27 is controlled via the transistor T2 and opens its contacts 27a and 27b. The contact 27a interrupts the voltage supply for the downward movement of the stand; the contact 27b interrupts the voltage supply for the upward movement of the operating table. In this way, the result is obtained that when the echo signal occurs within 1.2 ms and the distance between operating microscope and patient is thus less than 20 cm, no further reduction in distance between patient and operation microscope is possible any longer.

It is obvious that by a different dimensioning of the circuit one can operate with different frequencies and time intervals. The numerical values indicated are merely illustrative. The distance between patient and operation microscope below which no further reduction should be possible can be adjusted by the potentiometer P2 and thus adapted, for instance, to the focal length of the operation microscope used.

It is possible to place the ultrasonic device in operation only when a motor is connected in the direction of rotation for reduction of the distance between operation microscope and patient. Other electromotive movements such as, for instance, the focusing of the microscope 9 can also be included in the spacing safety mechanism.

What is claimed is:

1. A spacing safety mechanism for an operation microscope mounted on an electromotive stand with a motor drive for changing the position of said microscope, said safety mechanism comprising an ultrasonic transmitter (17) mounted on the microscope and an ultrasonic receiver (17') also mounted on the microscope, and an electronic unit (19), arranged on said stand and cooperating with said motor drive, for producing a signal for said ultrasonic transmitter and processing signals from said ultrasonic receiver.

2. The invention defined in claim 1, wherein said ultrasonic transmitter (17) and said ultrasonic receiver (17') are arranged on the bottom side (10') of the body (10) of said microscope.

3. The invention defined in claim 1, wherein said ultrasonic transmitter (17) and said ultrasonic receiver (17') are arranged on opposite sides of the body (10) of said microscope.

4. The invention defined in claim 1, wherein said ultrasonic transmitter (17) transmits signals having a duration of about 0.25 ms at a frequency of about 40 kHz and at time intervals of about 25 ms.

5. A safety device for preventing accidental contact of a medical appliance with a patient's body, said safety device comprising:
 (a) motor drive means for varying the distance from said medical appliance to said patient's body;
 (b) an ultrasonic transmitting unit;
 (c) an ultrasonic receiving unit for receiving signals transmitted by said transmitting unit;
 (d) said transmitting unit and receiving unit being so located and arranged that a signal transmitted by said transmitting unit impinges on said patient's body and is reflected from said body to said receiving unit;
 (e) at least one of said units being mounted in fixed relation to said medical appliance, whereby the time of travel of a given signal from said transmitting unit to said receiving unit varies in response to variations in distance from said appliance to said body;
 (f) electronic signal processing means responsive to signals received by said receiving unit; and
 (g) means responsive to said processing means for blocking operation of said motor drive means in a distance decreasing direction when the distance from said appliance to said body is at a predetermined minimum.

6. The invention defined in claim 5, wherein both said transmitting unit and said receiving unit are in fixed relation to said medical appliance.

7. The invention defined in claim 5, wherein said medical appliance is an operation microscope.

8. The invention defined in claim 5, wherein said motor drive means is operatively connected to said medical appliance to move said medical appliance with respect to said body.

9. The invention defined in claim 5, wherein said transmitting unit transmits signals having a duration of about 0.25 ms at a frequency of about 40 kHz and at time intervals of about 25 ms.

* * * * *